(12) United States Patent
Ahmed et al.

(10) Patent No.: US 10,751,294 B1
(45) Date of Patent: Aug. 25, 2020

(54) DEVELOPMENT OF AN OPTIMIZED AVANAFIL-LOADED INVASOMAL TRANSDERMAL FILM

(71) Applicant: King Abdulaziz University, Jeddah (SA)

(72) Inventors: Osama A. A. Ahmed, Jeddah (SA); Shaimaa M. Badr-Eldin, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

(21) Appl. No.: 16/675,648

(22) Filed: Nov. 6, 2019

(51) Int. Cl.
| | | |
|---|---|---|
| A61K 47/10 | (2017.01) | |
| A61K 9/70 | (2006.01) | |
| A61K 31/506 | (2006.01) | |
| A61K 47/24 | (2006.01) | |
| A61K 9/00 | (2006.01) | |
| A61K 47/69 | (2017.01) | |

(52) U.S. Cl.
CPC .......... *A61K 9/7023* (2013.01); *A61K 9/0014* (2013.01); *A61K 31/506* (2013.01); *A61K 47/10* (2013.01); *A61K 47/24* (2013.01); *A61K 47/6911* (2017.08)

(58) Field of Classification Search
None
See application file for complete search history.

(56) References Cited

U.S. PATENT DOCUMENTS

2003/0064948 A1* 4/2003 Fahr ................. A61K 9/127
514/44 A

FOREIGN PATENT DOCUMENTS

IN    201504226 I3  * 12/2017

OTHER PUBLICATIONS

Hosny et al. "Avanafil Liposomes as Transdermal Drug Delivery for Erectile Dysfunction Treatment: Preparation, Characterization, and In vitro, Ex vivo and In vivo Studies", Tropical Journal of Pharmaceutical Research Apr. 2015; 14 (4): 559-565 (Year: 2015).*

* cited by examiner

*Primary Examiner* — James W Rogers
(74) *Attorney, Agent, or Firm* — W&C IP (57) ABSTRACT

Nanosized avanafil (AVA) invasomes with enhanced transdermal delivery are provided. AVA invasomes were prepared with a vesicular size of 109.92 nm and an entrapment efficiency of 96.98%. The AVA invasomal film showed enhanced ex vivo permeation bioavailability compared to a raw AVA film.

17 Claims, 7 Drawing Sheets

DEVELOPMENT OF AN OPTIMIZED AVANAFIL-LOADED INVASOMAL TRANSDERMAL FILM

FIELD OF THE INVENTION

The invention is generally related to methods to prepare avanafil-loaded invasomal transdermal films. In particular, the film is useful for the enhancing the bioavailability of the erectile dysfunction drug avanafil.

BACKGROUND OF THE INVENTION

Avanafil (AVA) is a novel selective phosphodiesterase type 5 (PDE5) inhibitor. AVA attained FDA approval for treating erectile dysfunction in 2012 to be the fourth marketed PDE5 inhibitor (Bruzziches et al., 2013; Huang and Lie, 2013). AVA has a molecular weight of 483.951 g/mol and two pKa values, 11.84 (acidic) and 5.89 (basic). It has a log P value of 1.84, and consequently, it suffers from low solubility in water, methanol, and ethanol (<1 mg/mL at 25° C.) (Can, 2018; Soliman et al., 2017). AVA also suffers from considerable pre-systemic metabolism and altered absorption in the presence of food despite its rapid absorption upon oral administration. The aforementioned drawbacks result in limited oral bioavailability (Burke and Evans, 2012; European Medicines Agency, 2013; Fahmy et al., 2014; Katz et al., 2014).

Transdermal delivery represents a promising approach for the delivery of drugs undergoing first pass metabolism. It has the advantages of surmounting the first pass effect of the drugs compared to the conventional oral route and increasing patient compliance via convenient and painless administration compared to other invasive routes. In addition, it could provide controlled drug delivery and reduced side effects (Ahad et al., 2014; Alkilani et al., 2015; Lakshmi et al., 2013). However, the main obstacle for transdermal delivery is the reduced permeation of drugs owing to the natural barrier property of the outermost epidermal layer (stratum corneum). To circumvent this barrier, several approaches have been investigated including drug manipulation, modification of the stratum corneum through iontophoresis, and the utilization of chemical penetration enhancers and nanocarriers (Dragicevic et al., 2016). Lipid vesicular systems have been widely investigated for drug delivery via dermal and transdermal routes (Ashtikar et al., 2016). They could effectively enhance cutaneous drug accumulation; however, several studies demonstrated they had only limited ability to deliver the drug effectively across the skin (Mura et al., 2009; Romero and Morilla, 2013). Accordingly, the researchers directed their focus towards the development of new generations of flexible lipid vesicular systems including transferosomes, ethosomes, and more recently, invasomes (Badr-Eldin and Ahmed, 2016; Mahmood et al., 2018; Shah et al., 2015).

Invasomes are innovative elastic vesicles comprising phosphatidylcholine, ethanol, and terpene(s). They exhibit improved cutaneous and percutaneous absorption of aqueous and lipid soluble drugs compared to conventional liposomes (Dragicevic-Curic et al., 2008; Dwivedi et al., 2017). Terpenes could potentially enhance drug penetration through disrupting the tight lipid packing of the epidermal layer (stratum corneum) and interacting with intracellular proteins (Aqil et al., 2007; Yang et al., 2013). Ethanol enhances the penetration through the stratum corneum. Moreover, it supplies a net negative surface charge and protects against vesicle aggregation owing to electrostatic repulsion (El-Nabarawi et al., 2018; Paolino et al., 2005).

Several researchers have investigated invasomes as potential delivery systems for enhancing transdermal penetration of drugs. Ntimenou el al. (Ntimenou et al., 2012) reported the superiority of invasomes to enhance the skin permeation ability of drug molecules compared to other lipid vesicular systems. Minimal skin permeation of the model drug (calcein) was observed from aqueous solution, whereas the drug permeation was slightly enhanced from conventional liposomes and enhanced by 1.8 and 7.2 fold from transfersomes and invasomes, respectively.

SUMMARY OF THE INVENTION

An aspect of this invention provides avanafil invasomes (AVA invasomes) and method of preparing the AVA invasomes. The system described herein provides a delivery mechanism for avanafil for a more effective treatment of erectile dysfunction. An embodiment of the inventions provides a method of forming AVA invasomes having high entrapment efficiency which increase penetration through the skin.

In some embodiments, AVA invasomes are produced by mixing phosphatidylcholine, ethanol, a terpene and avanafil. In a further embodiment, the proportion of the phosphatidylcholine is present in a range of 6-14 wt. %. In a further embodiment, the proportion of ethanol is in a range of 2.0 to 5.0 wt. %. In yet another embodiment, the proportion of the terpene is in a range of 1.0 to 1.5 wt. %.

In some embodiments, the terpene is β-citronellol, with a proportion of 1.0, 1.25 or 1.5 wt. %.

In some embodiments, the terpene is D-limonene with a proportion of 1.0, 1.25 or 1.5 wt. %.

In another aspect, the AVA invasomes are formulated for application to the skin. In some embodiments, the AVA invasomes are used for treating erectile dysfunction (ED) in a subject in need thereof by administrating a therapeutically effective quantity of AVA invasomes through the skin.

DESCRIPTION OF THE DRAWINGS

FIG. 2 A-F. Three-dimensional surface and interaction plots for the effects of concentration on the vesicle size of avanafil invasomes: A. ethanol %, PL %, B. terpene %, PL %, C. terpene %, ethanol %, D. terpene type and % PL, E. terpene type and % ethanol, F. terpene type and % terpene.

FIG. 3 A-F. Three-dimensional surface and interaction plots for the effects of concentration on entrapment efficiency of avanafil invasomes: A. ethanol %, PL %, B. terpene %, PL %, C. terpene %, ethanol %, D. terpene type and % PL, E. terpene type and % ethanol, F. terpene type and % terpene.

FI highest $R^2$ for entrapment efficiency was the linear model (Table 1). FIG. 3 illustrates the effect of the independent variables on the entrapment efficiency, $Y_2$.

The increase in the entrapment efficiency with increasing PL % could be ascribed to the lipophilic properties of AVA. Being a lipophilic drug, AVA is expected to be entrapped in the lipid phase. Using increasing amounts of phospholipids leads to an increase in the number of lipid particles forming each vesicle, thus increasing the chance of the drug to integrate with the lipoidal content of the invasomes.

In addition, terpene % showed a direct relationship with the entrapment efficiency of AVA. The increased entrapment efficiency at higher terpene concentrations could be explained based on the lipophilicity and the molecular structure of the terpenes used In a preferred embodiment of the weight proportion of the phospholipids is in a range of about 6 to 14 wt. % such as about 6, 7, 8, 9, 10, 11, 12, 13 or 14 wt. %.

In a further preferred embodiment, the weight proportion of phosphatidylcholine is about 6-14 wt % e.g. about 6, 10 or 14 wt %, such as about 10 wt. %.

In a preferred embodiment, the weight proportion of ethanol is in a range of about 2 to 5 wt. % such as about 2, 2.5, 3, 3.5, 4, 4.5 or 5 wt. %.

In a further preferred embodiment, the weight proportion of ethanol is about 2.0, 3.5 or 5.0 wt. %.

In a preferred embodiment, the weight proportion of the terpenes is in a range of about 1 to 1.5 wt. % such as about 1, 1.25 or 1.5 wt. %.

In a further preferred embodiment, the wt % ranges and values are:

about 2 to 5 wt. % of ethanol such as about 2, 2.5, 3, 3.5, 4, 4.5 or 5 wt. % and about 1 to 1.5 wt. % of terpenes such as about 1, 1.25 or 1.5 wt. %.

In a further preferred embodiment, the terpene is β-citronellol or D-limonene.

In a further preferred embodiment, the weight proportion of the β-citronellol is about 1.0, 1.25 or 1.5 wt. %. In a further preferred embodiment, the weight proportion of D-limonene is about 1.0, 1.25 or 1.5 wt. %.

In one embodiment, the AVA invasomes have size in a range of from about 90 to 800 nm such as about 90, 100, 105, 110, 115, 120, 125, 130, 135, 140, 145, 150, 155, 160, 165, 170, 175, 180, 185, 190, 195, 200, 205, 210, 215, 220, 225, 250, 255, 260, 265, 270, 275, 280, 285, 290, 295, 300, 305, 310, 315, 320, 325, 350, 355, 360, 365, 370, 375, 380, 385, 390, 395, 400, 405, 410, 415, 420, 425, 450, 455, 460, 465, 470, 475, 480, 485, 490, 495, 500, 505, 510, 515, 520, 525, 550, 555, 560, 565, 570, 575, 580, 585, 590, 595, 600, 605, 610, 615, 620, 625, 650, 655, 660, 665, 670, 675, 680, 685, 690, 695, 700, 705, 710, 715, 720, 725, 750, 755, 760, 765, 770, 775, 780, 785, 790, 795 or 800 nm. The size of the AVA invasomes depends on the production methods and composition of the vesicles.

In another embodiment, the AVA invasomes have an entrapment efficiency in the range of about 75 to 100% such as about 75, 76, 77, 78, 79, 80, 81, 82, 83, 84, 85, 86, 87, 88, 89, 90, 91, 92, 93, 94, 95, 96, 97, 98, 99 or 100%.

Ex Vivo Permeation

Ex vivo permeation studies are regarded as a useful tool that provides insight into the performance of transdermal films under in vivo conditions. The mean cumulative percent AVA permeated from the optimized AVA invasomal film compared to the raw AVA film is graphically illustrated in FIG. 4. Statistical analysis revealed a significantly higher cumulative percent AVA permeated from the optimized invasomal films relative to the raw AVA films ($p<0.05$). The permeation parameters of AVA from the raw and optimized invasomal films presented in Table 2 show higher permeability and diffusion coefficients from the invasomal film compared to the raw AVA film. The computed enhancement factor for the cumulative amount of drug permeated from the optimized invasomal film was 2.514 relative to the raw AVA film. Invasomes could potentially penetrate the uppermost epidermal barrier and deeper dermal tissues into the systemic circulation due to their reported deformability and ultraflexibility. The penetration ability of invasomes could be due to the synergistic effect of both ethanol and terpenes as penetration enhancers. Ethanol has the ability to disrupt the skin lipid bilayer organization and increases its fluidity through its interaction with the polar head region of the stratum corneum lipid molecules. In addition, owing to the presence of ethanol, the lipid membrane is packed less tightly than in conventional vesicles, allowing a more flexible structure, and thus, a greater ability to "squeeze" through the small gaps created in the disordered stratum corneum lipid bilayer. Furthermore, terpenes could enhance drug permeation through interactions with cellular membrane proteins, reorganization of the lipid bilayer, and disruption of the stratum corneum barrier. The mechanism of barrier disruption might be explained on the basis of competitive hydrogen bonding of terpenes with the ceramides that could lead to interrupting the hydrogen bond network in the lipid bilayer of the stratum corneum and consequently enhancing drug permeation across it (Ahad et al., 2011; Dragicevic-Curic et al., 2009; Lakshmi et al., 2013; Qadri et al., 2017). The increased surface area could increase the contact with the stratum corneum cells, and consequently could increase the amount of drug permeated. The aforementioned results confirm the ability of invasomes to enhance the permeation of AVA through skin, and consequently highlight the possibility of improving its bioavailability via transdermal application.

TABLE 2

Ex vivo permeation parameters of transdermal film loaded with optimized AVA invasomes compared to raw AVA.

| Formulation | $D_{max}$ (μg) ± SD | $J_{ss}$ (μg/cm² h) | Pc (cm/h) × $10^2$ | D (cm²/h) × $10^2$ | Enhancement Factor |
|---|---|---|---|---|---|
| Optimized AVA invasomal film | 158.60 ± 10.95 | 3.42 | 1.51 | 0.98 | 2.514 |
| Raw AVA film | 63.09 ± 13.51 | 2.05 | 0.91 | 0.333 | — |

Abbreviations:
AVA, avanafil;
$D_{max}$, maximum amount of drug permeated;
Jss, steady-state flux;
Pc, permeability coefficient;
D, diffusion coefficient;
SD, standard deviation.

In Vivo Pharmacokinetic Studies In some aspects, AVA invasomes are produced for topical application of avanafil to enhance the bioavailability of the drug to treat erectile dysfunction.

Figure 1A:
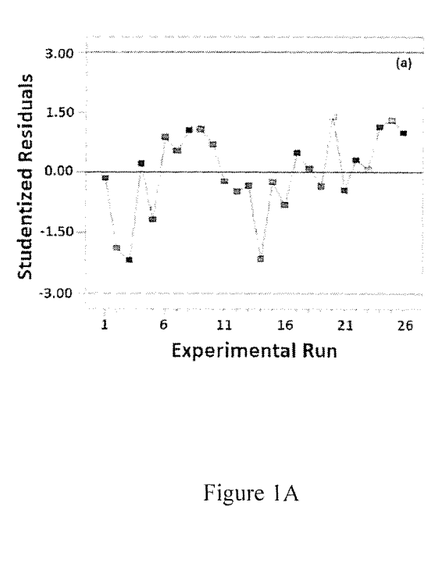
FIG. 1A-B. Residual plots for the observed and predicted responses of avanafil invasomes prepared according to a Box-Behnken design; A, vesicle size and B, entrapment efficiency.
Figure 1B:
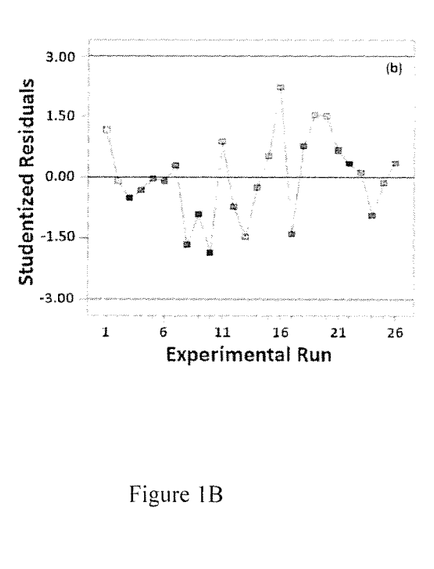
Figure 2A:
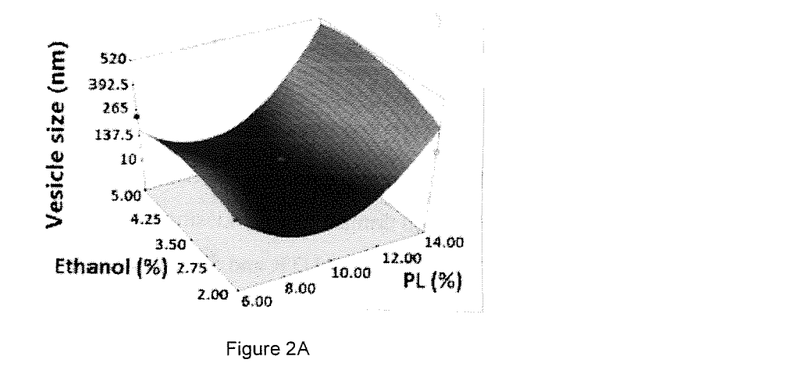
Figure 2B:
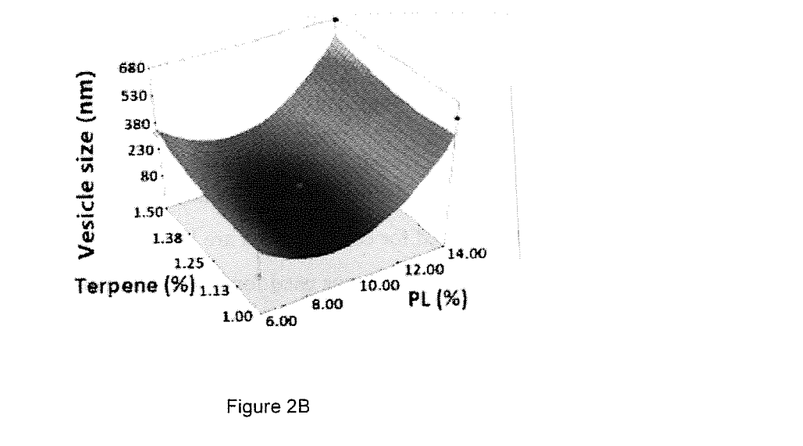
Figure 2C:
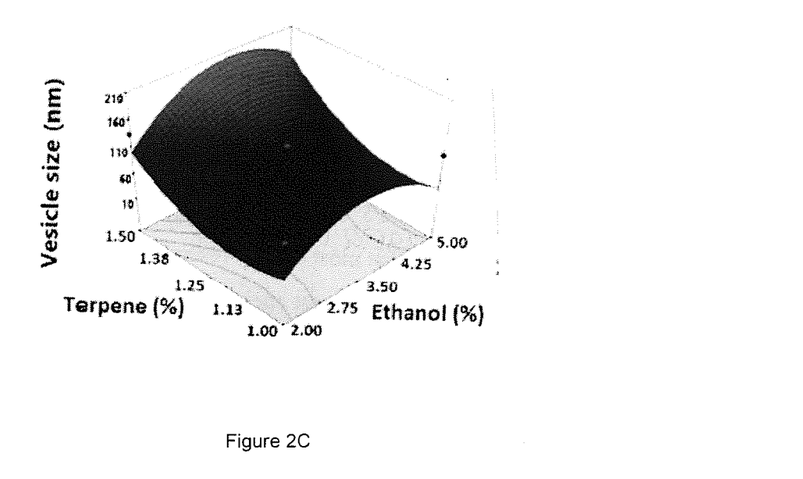
Figure 2D:
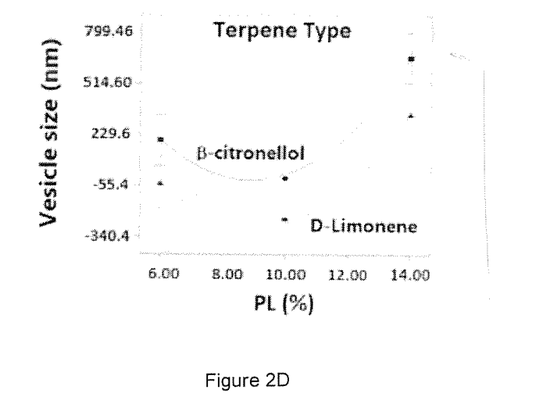
Figure 2E:
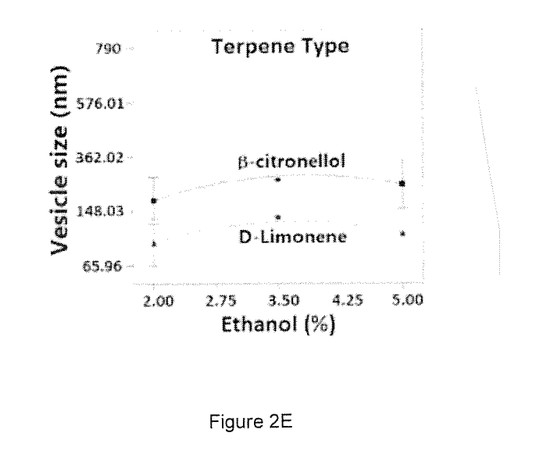
Figure 2F:
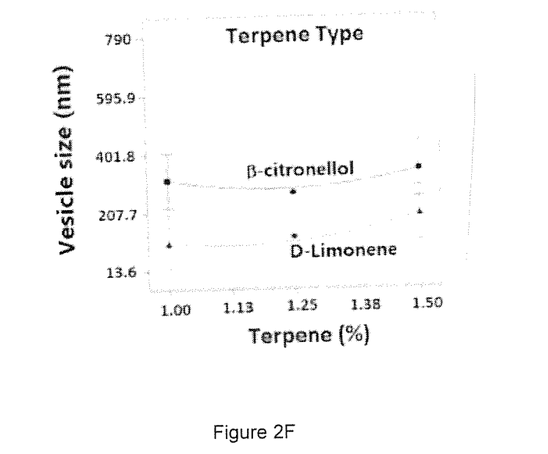
Figure 3A:
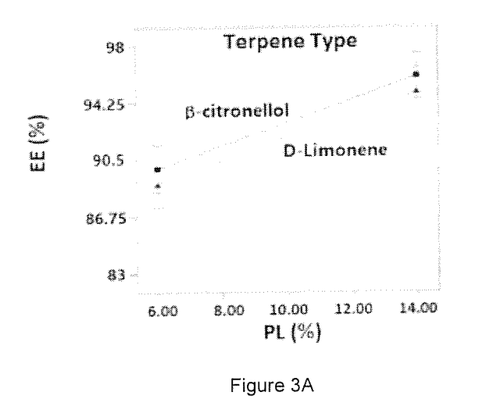
Figure 3B:
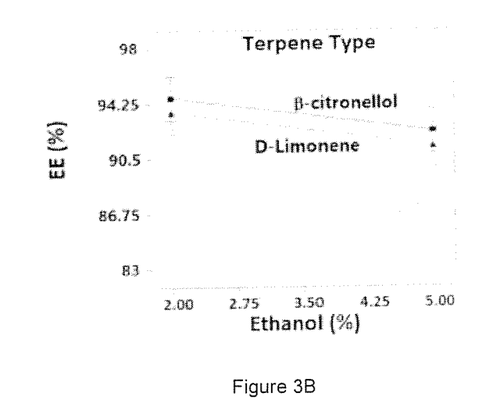
Figure 3C:
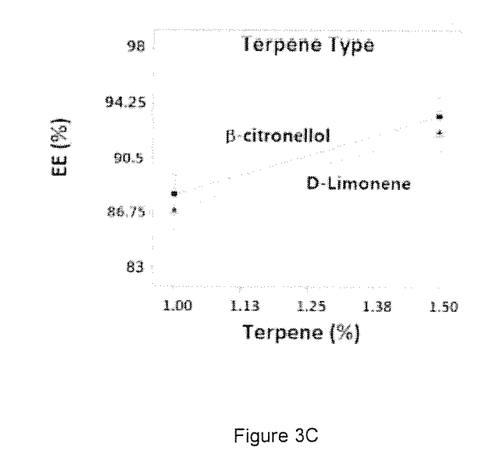
Figure 3D:
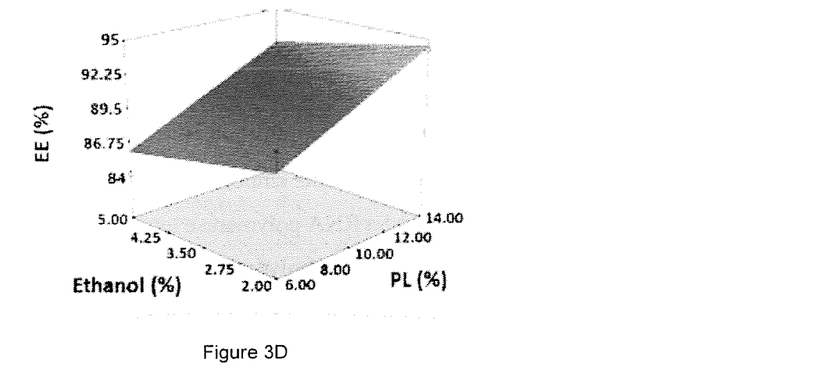
Figure 3E:
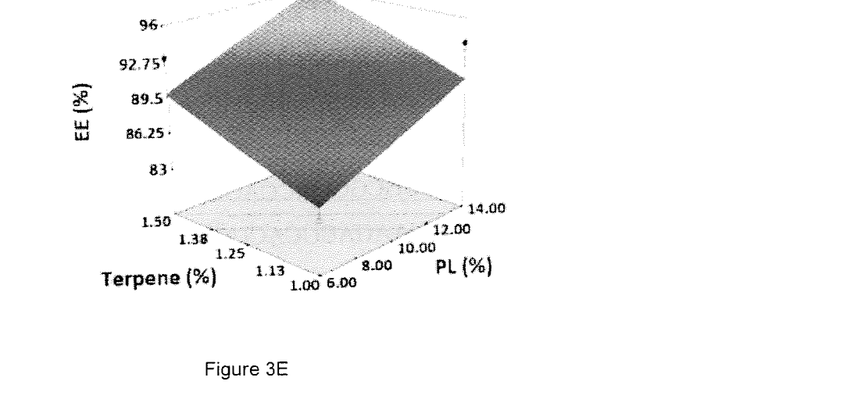
Figure 3F:
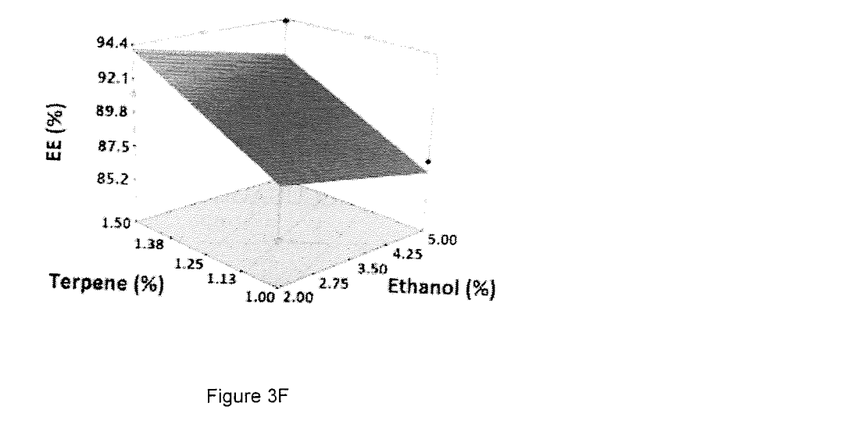
Figure 4:
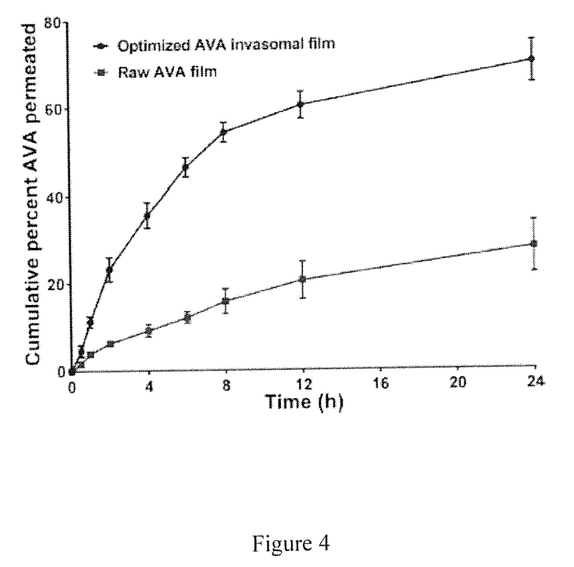
FIG. 4. Mean cumulative AVA percent permeated across excised rat abdominal skin from optimized AVA invasomal film compared to raw AVA film.
Figure 5:
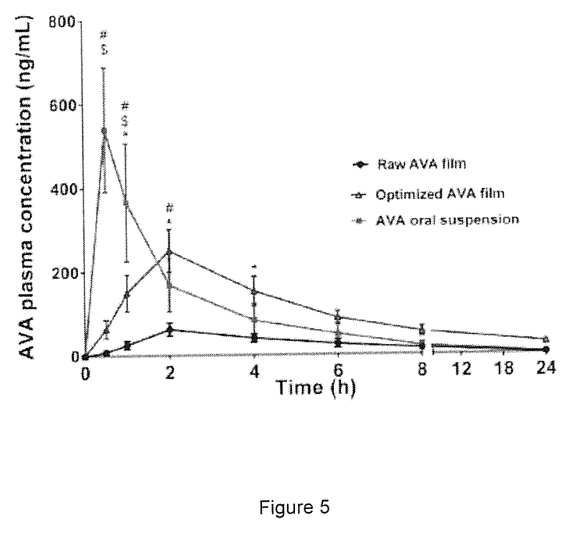
FIG. 5. Avanafil plasma concentration-time plot following transdermal application of optimized AVA invasomal transdermal film compared to raw AVA transdermal films and AVA suspension (administered orally). Data represent the mean value±standard deviation (SD), n=12. [#]Significant at P<0.05, for AVA oral suspension vs raw AVA transdermal films. [$]Significant at P<0.05, for optimized AVA invasomal transdermal film vs AVA oral suspension. *Significant at P<0.05, for optimized AVA invasomal transdermal film vs raw AVA transdermal films.

The mean concentrations of AVA in rats' plasma following oral administration of AVA suspension and transdermal application of raw AVA films and optimized AVA invasomal films are graphically illustrated in FIG. 5. Compared to the oral suspension, the optimized AVA invasomal film demonstrated a significantly higher AUC ($P<0.05$) with a relative bioavailability of 148.5% (Table 3). The increased bioavailability from the invasomal transdermal films could be due to bypassing the presystemic metabolism of the drug. The lower $C_{max}$ and longer $T_{max}$ demonstrated by the optimized films compared to the oral suspension might be attributed to the ability of the invasomes to control AVA release and consequently its absorption.

In addition, the optimized AVA invasomal film demonstrated significantly higher $C_{max}$ and AUC ($P<0.05$) relative to the raw AVA film with a relative bioavailability of 451.44% (Table 4). Both films reached maximum plasma concentrations after a median time of 2 h. The increased absorption extent of the drug following transdermal application of the optimized AVA invasomal film could be credited to the enhanced permeation of the drug from invasomes as confirmed by the ex vivo studies. The presence of terpenes that disrupt the stratum corneum lipid packing and ethanol that acts as a permeation enhancer and imparts flexibility to the vesicles, in addition to the nanometric size of the vesicle that increases the surface area interacting with the corneocytes, could dramatically contribute to the penetration enhancing ability of invasomes.

TABLE 3

In vivo pharmacokinetic parameters following transdermal application of optimized AVA invasomal films, raw AVA films and oral AVA suspension.

| Pharmacokinetic parameter | Optimized AVA invasomal film | Raw AVA film | Oral AVA suspension |
|---|---|---|---|
| $C_{max}$(ng/mL) | 250.392 ± 50.848*# | 62.691 ± 15.559 | 539.413 ± 148.953 |
| $t_{max}$ (h) | 2 | 2 | 0.5 |
| $AUC_{(0-24)}$ (ng · h/mL) | 1717.036 ± 311.276* | 403.729 ± 122.461 | 1273.478 ± 457.806 |
| $AUC_{(0-\infty)}$ (ng · h/mL) | 2055.063 ± 213.381*# | 425.462 ± 125.237 | 1293.383 ± 467.062 |
| $AUMC_{(0-\infty)}$ ng · $hr^2$/mL | 20574.508 ± 2185.174*# | 2911.066 ± 954.809 | 4735.366 ± 1920.947 |
| MRT (h) | 10.085 ± 1.425*# | 6.797 ± 0.247 | 3.596 ± 0.391 |
| Relative bioavailability (%) | 451.44%§<br>148.5%$ | — | |

Data represent the mean value ± standard deviation (SD), n = 6

*Significant at $P < 0.05$, unpaired t test (two-tailed) with Welch's correction compared to raw film

Significant at $P < 0.05$, unpaired t test (two-tailed) with Welch's correction compared to oral suspension §Relative to raw film $Relative to oral suspension Films and Patches In some aspects, the disclosure provides films comprising the AVA invasomes described herein. The films generally range in size from about 4 to about 60 $cm^2$. The thickness of the films is generally in the range of from about 50 to about 250 μm.

The films generally comprise a single dose of AVA formulated within a matrix, such as a flexible, semi-solid polymer matrix. Those of skill in the art are familiar with materials which form matrices and that are suitable for use in transdermal drug delivery. Such materials are generally biocompatible and allow release of the AVA from the matrix onto/into the skin when the matrix comes into contact with the skin. Examples of suitable matrix-forming materials include but are not limited to: various hydrophilic and hydrophobic polymeric matrices, various plastic or synthetic resin matrices, pressure-sensitive adhesives (e.g. hydrophilic polyvinylpyrrolidone (PVP)-polyethylene oxide (PEO) based pressure sensitive adhesive (PSA) matrices), polymers based on acrylic acid and its esters, isobutylenes, ethylene-vinyl acetate copolymers, natural rubbers, synthetic rubbers, styrene-diene copolymers, styrene-butadiene block copolymers, isoprene block copolymers, acrylonitrile-butadiene rubber, butyl rubber and neoprene rubber, pressure sensitive adhesives based on silicone, various silicone materials and silicone elastomer blends, hot-melt adhesives, mixtures of esters of hydrogenated colophony with cellulose derivatives, and combinations thereof. In some aspects, the matrix is formed from or includes, e.g. hydroxy propyl methyl cellulose (HPMC), chitosan, Ammonio Methacrylate Copolymer Ph Eur RL 100, Ammonio Methacrylate Copolymer Ph Eur RS 100, etc. In some aspects, the matrix is formed from or includes HPMC.

The film also generally includes a plasticizer. Examples of suitable plasticizers include but are not limited to: propylene glycol, dibutyl phthalate, Bis(2-ethylhexyl)adipate (DEHA), dimethyl adipate (DMAD), monomethyl adipate (MMAD), dioctyl adipate (DOA), dibutyl sebacate (DBS), dibutyl maleate (DBM), diisobutyl maleate (DIBM), DEHP (ow molecular weight ortho-phthalate), DINP and DIDP (high molecular weight ortho-phthalates), various biocompatible plasticizers such as various monosaccharides, oligosaccharides, polyols, lipids, etc. In some aspects, the plasticizer is propylene glycol, glycerol or poly(ethylene glycol) (PEG).

In some aspects, the film is deposited, formed or coated on a substrate or support, such as an inert, impermeable substrate or support, to form a "patch". The patch is a skin-worn, dermal patch suitable for transdermal drug delivery. Typically the substrate is a substantially planar material that has an outer surface and an inner surface, and the film is deposited directly onto the inner surface. The inner surface of the substrate may also include, near its edges in areas that do not contain film, an adhesive material that permits the patch to stay in place on the skin during drug administration. The adhesive section(s) may be part of the underlying substrate, which is in and of itself adhesive, or an adhesive material may be added to the periphery of the inner surface of the substrate, outside the area which contains the film. Suitable substrate materials include but are not limited to: polyethylene terephthalate (PET), polyolefins, high-density polyethylene (HDPE), low-density polyethylene (LDPE), polypropylene (PP), polyurethanes (PU), polyether amides (PEA), ethylene vinyl acetate (EVA), or combinations thereof. Suitable adhesives include but are not limited to: acrylic, polyisobutylene, and silicone-based adhesives, various pressure sensitive adhesives, etc. and others known in the art.

In addition, before use, a patch may comprise a removable (detachable) protective backing or "release liner" on an outer surface of the film (the side opposite to the inner surface of the film, which is in contact with the substrate. Materials suitable for use as backing layers are well-known known in the art and can comprise films of polyester, polyethylene, vinyl acetate resins, ethylene/vinyl acetate copolymers, polyvinyl chloride, polyurethane, and the like, metal foils, non-woven fabric, cloth and commercially available laminates. A typical backing material has a thickness in the range of 2 to 1000 micrometers. For example, 3M's Scotch Pak™ 1012 or 9732 (a polyester film with an ethylene vinyl acetate copolymer heat seal layer), 9723 (a laminate of polyethylene and polyester), or CoTran 9720 (a polyethylene film) are useful in the transdermal drug delivery systems described herein, as are Dow™ backing layer films, such as Dow™ BLF 2050 (a multi-layer backing comprising ethylene vinyl acetate layers and an internal SARAN™ layer), Bio-Release™, and Syl-Off™ 7610, Loparex's PET release liner (silicone-coated) and 3M's 1020, 1022, 9741, 9744, 9748, 9749 and 9755 Scotchpak™ (fluoropolymer-coated polyester films). When present, the release liner is removed (e.g. "peeled away") from the patch prior to use to expose the matrix layer and the adhesive layer prior to topical application.

The disclosure also encompasses a patch product comprising a patch as described herein, packaged (disposed, sealed, etc.) or provided within a pouch or sachet. The pouch is made of robust, impermeable material such as a foil or sturdy plastic, for example, DuPont's Surlyn™ can be used. Alternatively, a pouch comprising a coextruded ethylene acrylic acid/low-density polyethylene (EAA/LDPE) material, or Barex™ from INEOS (acrylonitrile-methyl acrylate) may be used. Prior to use the pouch is opened, the patch is removed from the pouch, the detachable backing is removed from the patch, and the patch is applied directly to the skin of the subject.

Additional options for materials and components that can be included in patches are described, for example, in issued U.S. Pat. Nos. 10,449,201; 10,251,834; 10,426,739; and 10,406,114; the complete contents of each of which are hereby incorporated by reference in entirety.

Figure 6A:
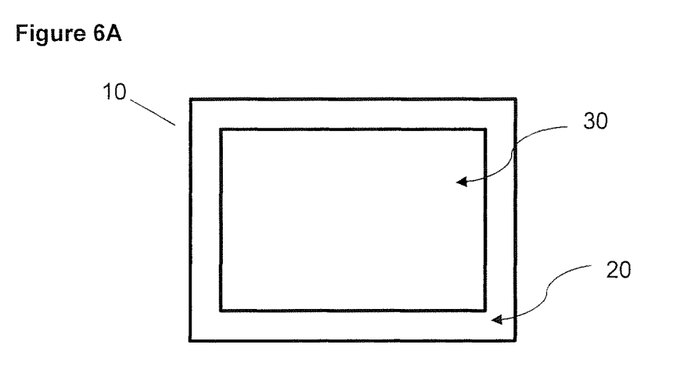
Figure 6B:
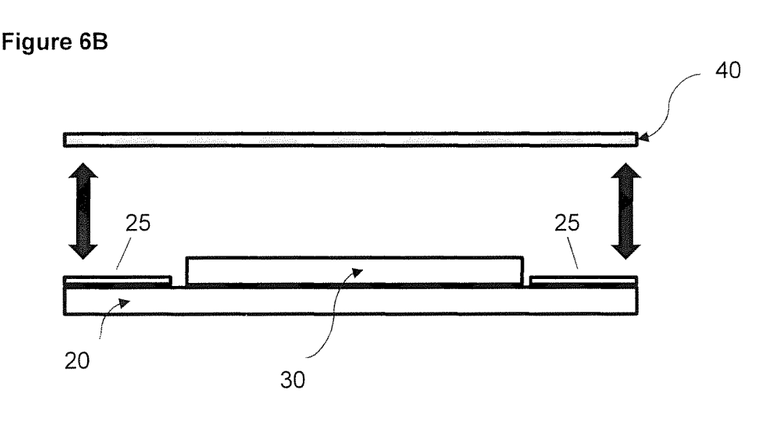

FIGS. 6A and B shows schematic representations of a patch comprising a film comprising the invasomes described herein. FIG. 6A shows a top view of patch 10 comprising substrate 20 and film 30 deposited (positioned) thereon. FIG. 6B shows a cross-sectional cut-away side view of patch 10 comprising substrate 20 and film 30 deposited (positioned) thereon. Also shown is release liner 40. The double-sided arrows illustrate that release liner 40 and be removably attached e.g. to adhesive area 25s at the peripheral edges of substrate 20.

Methods of Treating Erectile Dysfunction

The disclosure encompasses methods of treating erectile dysfunction in a subject in need thereof. The subject may be a human male or transgender individual. The methods involve administration, generally self-administration, of a film or patch of the invention to a skin surface of the subject. As described above, the patches generally have a peripheral adhesive area located at the edges of the patch, which ensure that the patch will stay in place during administration.

The currently recommended doses of AVA range from about 50 mg total per single dose to about 200 mg, such as e.g. 50, 100 or 200 mg. Generally, the drug is administered at most once per day before sexual activity, e.g. from about 15, 20 or 30 minutes before. Since the invasomes described herein provide an improved, more efficient method of administering the drug that is not prone to presystemic metabolism and altered absorption in the presence of food, in some aspects, the doses that are required are lower. For example, doses ranging from about 5 to about 50 mg per patch may be administered, such as about 5, 10, 15, 20, 25, 30, 35, 40, 45, or 50 mg per dose.

It is to be understood that this invention is not limited to particular embodiments described herein above and below, and as such may, of course, vary. It is also to be understood that the terminology used herein is for the purpose of describing particular embodiments only, and is not intended to be limiting.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

EXAMPLES

Materials.

AVA was kindly supplied by Jinlan-Pharm-Drugs Technology Co., Ltd. (Hangzhou, China). Terpenes (D-limonene & β-citronellol), hydroxy propyl methyl cellulose (HPMC), methanol and acetonitrile were purchased from Sigma-Aldrich (St. Louis, Mo., USA). Phospholipon® 90G (purified soybean lecithin with a phosphatidylcholine content of at least 90%) was purchased from Lipoid GmbH (Ludwigshafen, Germany).

Techniques.

Preparative HPLC was performed using Agilent 1260 Binary Pump comes with 1260 VWD (254 nm and 210 nm).

Dynamic light scattering technique was employed to measure the vesicular size (z-average) and polydispersity index (PDI) of the AVA invasomes (Zetatrac centrifuged at a speed of 20,000 rpm for 45 min (Sigma Lab, Model 3K30, Germany). The temperature was kept at 4° C. during centrifugation. Unentrapped AVA concentration was detected in the filtered supernatant after appropriate dilution using the reported HPLC method of Fahmy and Aljaeid (Fahmy and Aljaeid, 2016). The following equation was utilized to compute AVA % entrapped:

$$\% EE=[(C_a-C_b)/C_a]\times 100 \quad \text{Eq. (1)}$$

where $C_a$ and $C_b$ express the initial drug concentration and the unentrapped drug, respectively.

Example 4

The optimized AVA invasomal formulation was prepared and incorporated into hydroxypropyl methylcellulose (HPMC) transdermal films after assessing vesicular size and drug entrapment. Accurately weighed amounts of HPMC (2% w/v) as a matrix former and propylene glycol as a plasticizer were dispersed in distilled water. The AVA optimized invasomal formulation was gently stirred with the solution and then kept overnight at 4° C. for the gel to clear. The gel was poured into 9 cm diameter petri dishes and left to dry at 40° C. The formed films were covered with a backing membrane and cut into 1 $cm^2$ strips containing invasomes with an AVA content equivalent to 1 mg/$cm^2$. The cut strips were kept in aluminum packaging in a desiccator over calcium chloride at room temperature to keep them away from humidity until further investigation (El-Say et al., 2015). Raw AVA films were prepared using the same method for comparison.

Example 5

An automated Franz diffusion cell in a vertical diffusion cell test system (MicroettePlus Hanson Research, CA, USA) was used to study the ex vivo AVA permeation from the optimized AVA invasomal films via excised abdominal Wistar rat skin compared to raw AVA films in triplicate. Occlusive diffusion was applied utilizing a Plexiglass cover. Full thickness skin squares with a side length of 2.5 cm were mounted between the compartments of the diffusion cell. The outermost epidermal and the dermis were facing the donor and the receptor compartments, respectively. The film strips (1.5×1.5 cm) were placed in direct contact with the skin in the donor compartment after being equilibrated in phosphate buffer saline at pH 7.4 for 15 min at 32° C. Then, 7 mL of PBS buffer was placed in the receptor chamber. The effective diffusional area was 1.76 $cm^2$. The temperature was kept at 32±0.5° C. and the agitation was set at a rate of 400 rpm. Specified aliquots, at preset time-intervals, were automatically withdrawn (Parhi and Suresh, 2016). The AVA content in the withdrawn samples was detected using the previously mentioned reported HPLC method (Fahmy and Aljaeid, 2016). Permeation parameters, namely, the steady state flux $J_{ss}$ (μg/$cm^2$.h), permeability coefficient Pc, and diffusion coefficient (D), were computed (Badr-Eldin and Ahmed, 2016).

Example 6

Pharmacokinetic assessment of optimized AVA invasomal film following transdermal application was carried out in male Wistar rats (n=36), weighing≈220 g each, compared to raw AVA transdermal films and AVA oral suspension at a dose of 30 mg/kg. The protocol of the experiment was approved by the Research Ethics Committee, Faculty of Pharmacy, King Abdulaziz University, KSA. The committee affirmed that animal use complied with the Guiding Principles in the Care and Use of Animals (DHEW publication NIH 80-23). The rats were divided equally into three groups and fasted overnight before the experiment. Group I (standard control) received the AVA suspension orally. Raw AVA films and optimized AVA invasomal films were transdermally applied to group II (positive control) and group III (test), respectively. The applied films were occluded with adhesive patches. Blood samples were withdrawn via the tail vein at predetermined time intervals for 24 h after application. Plasma was obtained by centrifugation of blood samples at 3000 rpm for 8 min and stored at −80° C. until analysis using the modified HPLC method previously reported by Fahmy et al. (Fahmy et al., 2014) and validated in our laboratory. An isocratic mobile phase was utilized that comprised a mixture of acetonitrile and 10 mM ammonium acetate at a ratio of 3:2 v/v adjusted to pH 3. The HPLC assay was coupled with mass detection using multiple reactions monitoring scan mode performed at the reported m/z 484→383 for AVA.

Non compartmental analysis was applied to analyze the plasma data to compute different pharmacokinetic parameters using PK-SOLVER. The computed parameters were statistically analyzed using unpaired t tests (two-tailed) at $P<0.05$.

REFERENCES

[1] Ariza, E.; Chaves-Guerrero, A.; Molina V, D., Effect of Average Molecular Parameters of Asphaltenes on the Rheological Properties of Crude Oils from Colorado Oil Field. *Energy & Fuels* 2018, 32 (6), 6557-6564.

[2] Groenzin, H.; Mullins, O. C., Molecular Size and Structure of Asphaltenes from Various Sources. *Energy & Fuels* 2000, 14 (3), 677-684.

[3] Islam, M. R.; Hao, Y.; Wang, M.; Chen, C.-C., Prediction of Asphaltene Precipitation in Organic Solvents Via Cosmo-Sac. *Energy & Fuels* 2017, 31 (9), 8985-8996.

[4] Durand, E.; Clemancey, M.; Lancelin, J.-M.; Verstraete, J.; Espinat, D.; Quoineaud, A.-A., Aggregation States of Asphaltenes: Evidence of Two Chemical Behaviors by 1 h Diffusion-Ordered Spectroscopy Nuclear Magnetic Resonance. *The Journal of Physical Chemistry C* 2009, 113 (36), 16266-16276.

[5] Abedini, A.; Ashoori, S.; Torabi, F.; Saki, Y.; Dinarvand, N., Mechanism of the Reversibility of Asphaltene Precipitation in Crude Oil. *Journal of Petroleum Science and Engineering* 2011, 78 (2), 316-320.

[6] Paridar, S.; Solaimany Nazar, A. R.; Karimi, Y., Experimental Evaluation of Asphaltene Dispersants Performance Using Dynamic Light Scattering. *Journal of Petroleum Science and Engineering* 2018, 163, 570-575.

[7] Bai, L.; Nie, Y.; Li, Y.; Dong, H.; Zhang, X., Protic Ionic Liquids Extract Asphaltenes from Direct Coal Liquefaction Residue at Room Temperature. *Fuel Processing Technology* 2013, 108, 94-100.

[8] Hu, Y-F.; Guo, T.-M., Effect of the Structures of Ionic Liquids and Alkylbenzene-Derived Amphiphiles on the Inhibition of Asphaltene Precipitation from Co2-Injected Reservoir Oils. *Langmuir* 2005, 21 (18), 8168-8174.

[9] Ogunlaja, A. S.; Hosten, E.; Tshentu, Z. R., Dispersion of Asphaltenes in Petroleum with Ionic Liquids: Evaluation of Molecular Interactions in the Binary Mixture. *Industrial & Engineering Chemistry Research* 2014, 53 (48), 18390-18401.

[10] Boukherissa, M.; Mutelet, F.; Modarressi, A.; Dicko, A.; Dafri, D.; Rogalski, M., Ionic Liquids as Dispersants of Petroleum Asphaltenes. *Energy & Fuels* 2009, 23 (5), 2557-2564.

[11] Yakubov, M. R.; Gryaznov, P. I.; Yakubova, S. G.; Tazeeva, E. G.; Mironov, N. A.; Milordov, D. V., Structural-Group Composition and Properties of Heavy Oil Asphaltenes Modified with Sulfuric Acid. *Petroleum Science and Technology* 2016, 34 (22), 1805-1811.

[12] Jerome Panzer, R. P., N. J. Combination of Asphaltenes with Flow Improver Polymers to Improve the Flow Properties of High Boiling Fuel Oils. U.S. Pat. No. 4,074,978 (A), 1978.

[13] Pieter Marinus Willem Cornelisse, A. N. Method for Solubilising Asphaltenes in a Hydrocarbon Mixture. U.S. Pat. No. 7,122,113 B2, 2006.

[14] William K. Stephenson, S. M. K., Houston, both of Tex Asphaltene Dispersants Inhibitors. U.S. Pat. No. 5,021, 498, 1991.

[15] Daniel E. Bowen, I., Olathe, K S, US Asphaltenes-Based Polymer Nano-Composites. US 2012/0238669 A1, 2012.

[16] Armin C. Pitchford, B., Okla, Phillips Petroleum Company Asphaltene-Derived Surfactant Composition and Its Preparation. U.S. Pat. No. 3,646,120, 1972.

[17] Abdullah, M. M. S.; Al-Lohedan, H. A.; Atta, A. M., Novel Magnetic Iron Oxide Nanoparticles Coated with Sulfonated Asphaltene as Crude Oil Spill Collectors. *RSC Advances* 2016, 6 (64), 59242-59249.

[18] Siski, n M.; Francisco, M. A.; Billimoria, R. M. U.S. Pat. No. 8,734,639 B2, 2014.

[19] Weers, J.; Nguyen, H.;. Jen-Nings, D.; Chao, K-P. WO2019/113513 A1, 2019.

[20] Castro, L. V.; Vazquez, F., Fractionation and Characterization of Mexican Crude Oils. *Energy & Fuels* 2009, 23 (3), 1603-1609.

[21] Goual, L.; Sedghi, M., Role of Ion-Pair Interactions on Asphaltene Stabilization by Alkylbenzenesulfonic Acids. *Journal of Colloid and Interface Science* 2015, 440, 23-31.

[22] Murillo-Hernández, J. A.; Garcia-Cruz, I.; López-Ramirez, S.; Duran-Valencia, C.; Domínguez, J. M.; Aburto, J., Aggregation Behavior of Heavy Crude Oil-Ionic Liquids Solutions by Fluorescence *Spectroscopy. Energy & Fuels* 2009, 23 (9), 4584-4592.

[23] Atta, A. M.; Ezzat, A. O.; Abdullah, M. M.; Hashem, A. I., Effect of Different Families of Hydrophobic Anions of Imadazolium Ionic Liquids on Asphaltene Dispersants in Heavy Crude Oil. *Energy & Fuels* 2017, 31 (8), 8045-8053.

We claim:

1. A nano scale invasome vesicle composition comprising,
   phosphatidylcholine,
   ethanol,
   a terpene; and
   avanafil,
   wherein,
   phosphatidylcholine has a proportion of 6-14 weight %;
   ethanol has a proportion of 2.0-5.0 weight %; and
   the terpene has a proportion of 1.0 to 1.50 weight %;
   and wherein the phosphatidylcholine, the ethanol, the terpene and the avanafil combine to form nano scale invasome vesicles, wherein the nano scale invasome vesicles have a size in the range of from 90 to 800 nm, and wherein the nano scale invasome vesicle composition is configured for systemic delivery.

2. The nano scale invasome vesicle composition of claim 1, wherein the terpene is β-citronellol or D-limonene.

3. The nano scale invasome vesicle composition of claim 1, wherein the phosphatidylcholine has a proportion of 6, 10 or 14 weight %.

4. The nano scale invasome vesicle composition of claim 1, wherein the ethanol has a proportion of 2.0, 3.5 or 5.0 weight %.

5. The nano scale invasome vesicle composition of claim 1, wherein the terpene is β-citronellol having a proportion of 1.25 or 1.5 weight %.

6. The nano scale invasome vesicle composition of claim 1, wherein the terpene is D-limonene having a proportion of 1.0, 1.25 or 1.5 weight %.

7. The nano scale invasome vesicle composition of claim 5, wherein the ethanol has a proportion of 2.0 weight %, the terpene has a proportion of 1.5 weight %, wherein the terpene is D-limonene, and the phosphatidylcholine has a proportion of 10.47 weight %.

8. The nano scale invasome vesicle of claim 6, wherein the ethanol has a proportion of 2.0, 3.5 or 5.0 weight % and the phosphatidylcholine has a proportion of 6, 10 or 14 weight %.

9. The nano scale invasome vesicle composition of claim 1, wherein the nano scale invasome vesicle is formulated for systemic delivery through the skin.

10. A method of treating erectile dysfunction (ED) in a subject in need thereof, comprising
    administering through the skin of the subject a quantity of the nano scale invasome vesicle composition of claim 1 sufficient to treat ED in the subject.

11. A film comprising
    at least one matrix former,
    at least one plasticizer and
    the nano scale invasome vesicle composition of claim 1.

12. A transdermal patch comprising
    an impermeable substrate and
    a film deposited on the impermeable substrate, wherein the film comprises
        at least one matrix former,
        at least one plasticizer and
        the nano scale invasome vesicle composition of claim 1.

13. A transdermal patch product comprising
    an impermeable pouch and
    the transdermal patch of claim 12 sealed within the impermeable pouch.

14. A method of making an invasome materials comprising the steps of
    combining into a formulation
    phosphatidylcholine,
    ethanol,
    a terpene; and
    avanafil,
    wherein,
    phosphatidylcholine has a proportion of 6-14 weight %,
    ethanol has a proportion of 2.0-5.0 weight %; and
    the terpene has a proportion of 1.0 to 1.50% weight %, and
    forming invasomes from the formulation.

15. The method of claim 14 further comprising preparing a film from the formulation.

16. The method of claim 15 wherein the film is applied to a substrate.

17. The nano scale invasome vesicle composition of claim 1, which has an entrapment efficiency in the range of 75 to 100%.

\* \* \* \* \*